(12) United States Patent
Muckenhirn

(10) Patent No.: US 7,735,997 B2
(45) Date of Patent: Jun. 15, 2010

(54) RIGID CONTACT LENS

(75) Inventor: Dieter Muckenhirn, Wittnau (DE)

(73) Assignee: Hecht Contactlinsen GmbH, Au (DE)

( * ) Notice: Subject to any disclaimer, the term of this patent is extended or adjusted under 35 U.S.C. 154(b) by 267 days.

(21) Appl. No.: 11/508,330

(22) Filed: Aug. 23, 2006

(65) Prior Publication Data
US 2007/0046894 A1   Mar. 1, 2007

(30) Foreign Application Priority Data
Aug. 24, 2005   (EP) .................................. 05018424

(51) Int. Cl.
*G02C 7/04* (2006.01)

(52) U.S. Cl. ............... 351/160 R; 351/161; 351/160 H; 351/159

(58) Field of Classification Search .............. 351/160 R
See application file for complete search history.

(56) References Cited

U.S. PATENT DOCUMENTS 5,347,326 A    9/1994  Volk
5,517,260 A *  5/1996  Glady et al. ................ 351/169
5,695,509 A * 12/1997  El Hage ...................... 606/166
6,457,826 B1* 10/2002  Lett ............................ 351/161
6,474,814 B1* 11/2002  Griffin ........................ 351/161
6,599,285 B1*  7/2003  Lieberman et al. ............ 606/5
2002/0159025 A1 10/2002 Legerton et al.
2003/0175259 A1  9/2003  Karageozian et al.
2004/0257524 A1 12/2004 Tung

FOREIGN PATENT DOCUMENTS

WO        WO 9507487       3/1995

\* cited by examiner

*Primary Examiner*—Jessica T Stultz
(74) *Attorney, Agent, or Firm*—Millen, White, Zelano & Branigan, P.C.

(57) ABSTRACT

A rigid contact lens is provided for correcting an irregularly curved cornea, comprising a front surface (2) and a rear surface which consists of (3) a central optical zone (4) and a peripheral zone (5). The central optical zone (4) has such an aspherical rotationally symmetric or non-rotationally symmetric design that, with equal central curvature radius in the center (Z) of the central optical zone (4), the sagittal depth ($S_{ellip}$) of the central optical zone (4) is increased as compared with a spherical optical zone.

13 Claims, 4 Drawing Sheets

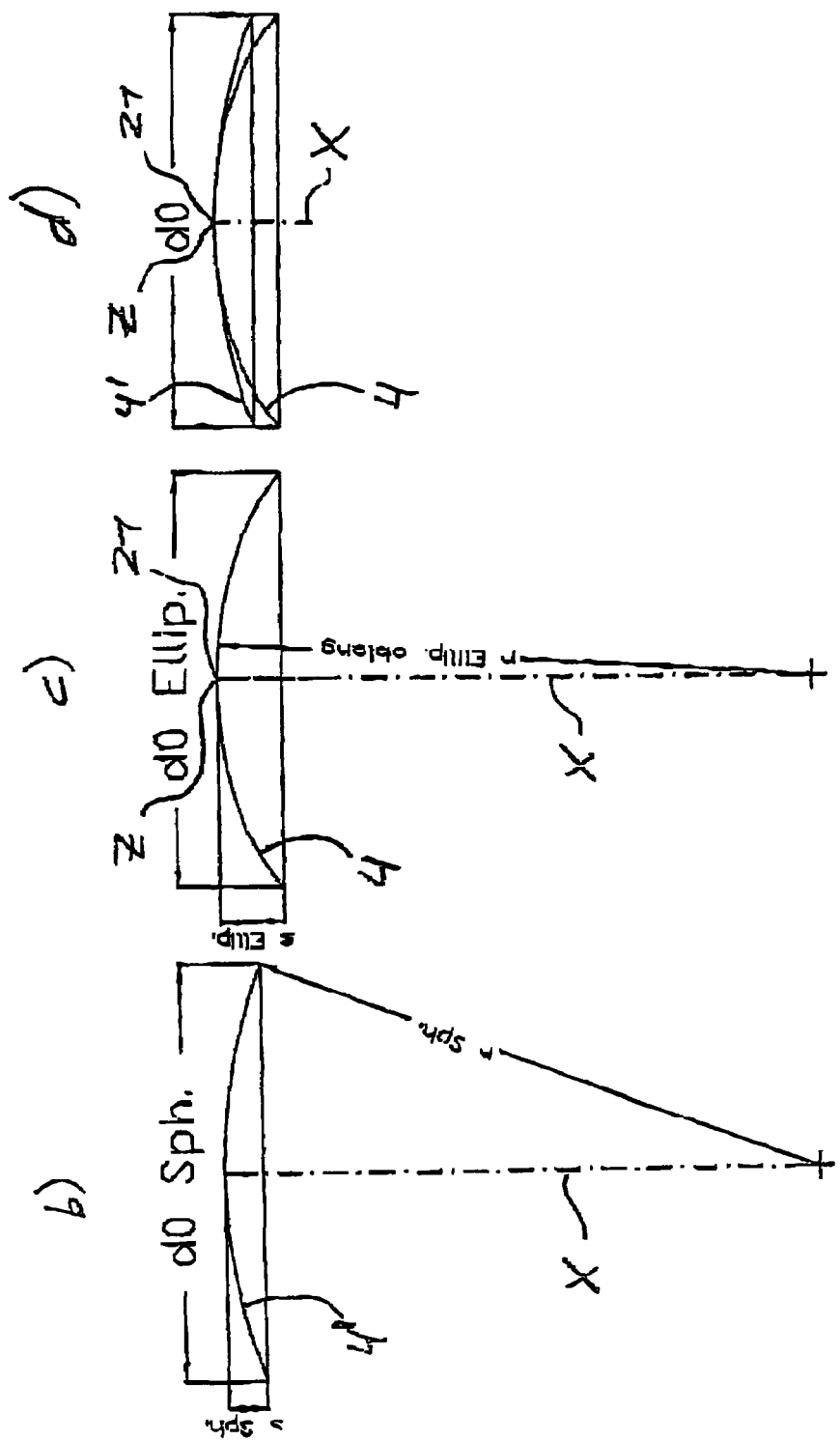

RIGID CONTACT LENS

Figure 7:
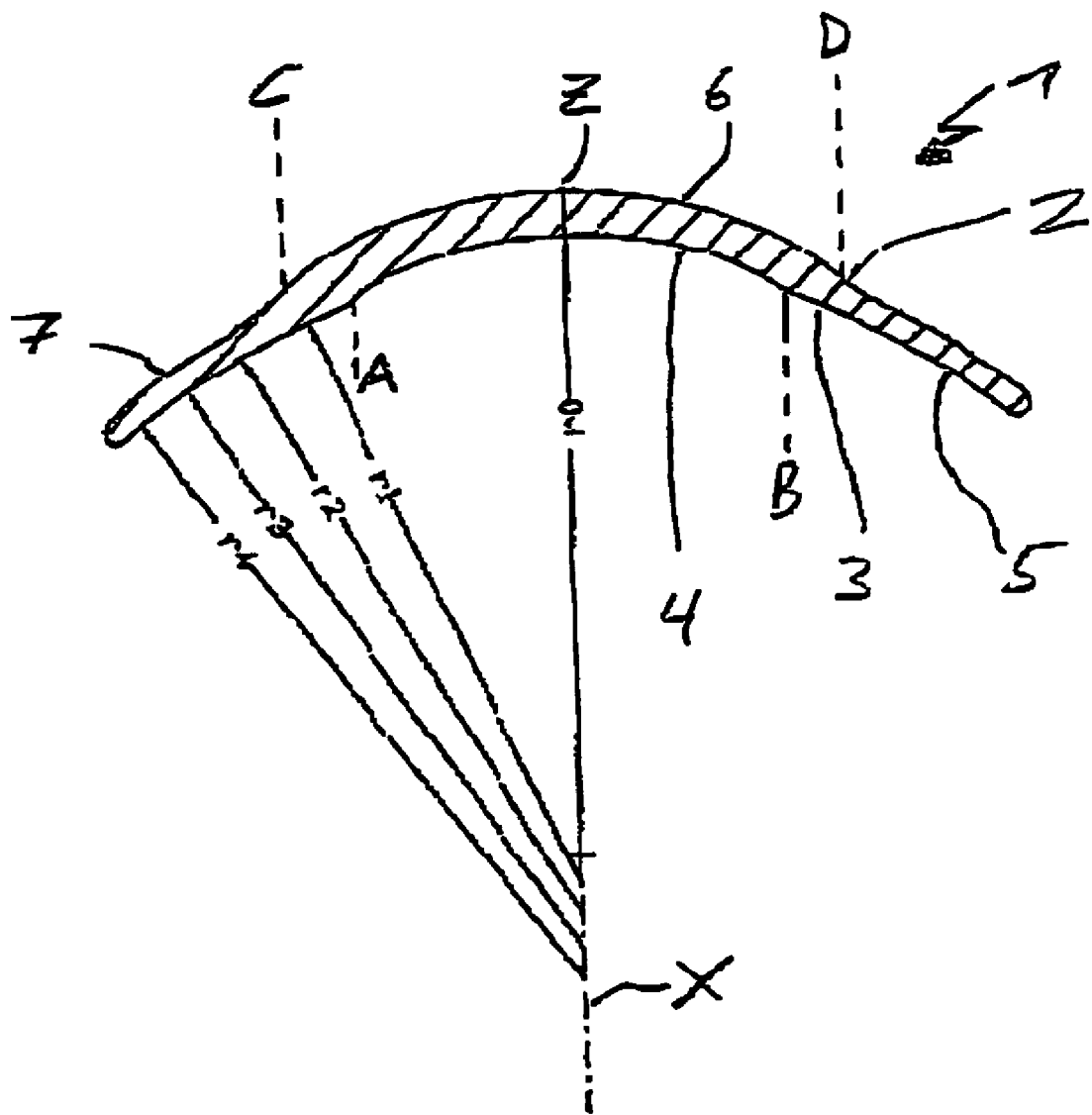

The present invention relates to a rigid contact lens, and particularly to a contact lens for correcting visual losses in keratoconus and other cases as well as for bridging central corneal epithelial defects.

There are various known technical procedures for the correction of visual losses. The most frequently used procedures are the fitting of spectacles and the fitting of contact lenses.

There are people among the population who suffer from keratoconus, that is a change in the structure of the corneal tissue where parts of the cornea are protruding. Furthermore, there are persons who, due to other conditions, suffer from a formation of central corneal scars resulting in a permanent central epithelial defect. In most of these cases, it is not possible to correct these persons' visual losses by means of spectacle glasses to a satisfactory degree. For that reason, use is frequently made of contact lenses to correct such visual losses.

Contact lenses, however, cannot be used without any difficulties either because, in the most cases, a rotationally symmetric or toric surface is placed onto the irregular corneal surface. Therein, too flatly fitted conventional contact lenses frequently and particularly pose the problem of an excessive mechanical pressure being exerted on the irregular corneal surface. This may result in a deteriorated state of the cornea and is also felt to be painful by the persons wearing the contact lenses. Usually, these known contact lenses are fitted according to a three-point touch method or according to a contour technique with apical bridging.

In order to bypass the problem of the high mechanical pressure on the irregular corneal surface, use is made of contact lenses which, in the central optical zone on their rear surface that is facing the eye, comprise a spherical surface with a radius that is less than that of the irregular corneal surface. Such a contact lens is, for example, described in EP 0 235 328 B1. Therein, bridging of the sensible central corneal zone is achieved. However, this procedure is to disadvantage in that, as a result of the reduction in radius of the central optical zone on the rear surface that is facing the eye, the optical effect of the contact lens must become considerably stronger for thickness compensation purposes, said reduction in radius being, in part, very pronounced. For example, the thickness of a fully corrected contact lens having a radius of $r_0$=6.5 mm and −10.00 dpt changes to −14.25 dpt when the radius is changed to $r_0$=6.00 mm. Although such a steeper lens has the same optical effect on the eye, the visual acuity of the person wearing the contact lens becomes markedly worse, as has been described in literature (Zadnik, K.; Mutti, D. O.; American Journal of Optometry and Physiological Optics, September 1987, 698ff.). Often, the person wearing the contact lens even desires a higher dioptric value than that calculated from the change in radius.

EP 0 722 573 B1 has disclosed a contact lens which comprises on its side facing the eye a spherical central optical section to which is adjoining an aspherical peripheral region which is adjusted to the shape of the cornea. This contact lens results in the problems described above.

The present invention aims at creating a contact lens which allows a reduction of the load applied to an irregular corneal surface while, at the same time, achieving a good or improved visual acuity.

This problem is solved by a rigid contact lens according to Claim 1. Further developments of the invention are characterized in the subordinate claims.

With the contact lens according to the invention, it is achieved that the sagittal depth of the central optical zone is increased as compared with a conventional spherical or toric central optical zone, thus allowing bridging of an irregular region of the cornea while, at the same time, allowing selection of a central curvature radius in the center of the central optical zone in the same manner as for a contact lens for a regular cornea. Hence, if it is intended to bridge an irregular region of the cornea, it is not necessary to increase the thickness of the contact lens.

Thus, the structure according to the invention permits to adjust the rear surface of the contact lens such that it meets the contour of an irregular cornea. This reduces or eliminates the latter's mechanical pressure load, and the contact lens represents a least possible physiological load. As a result, the visual capacity of the eye is not worsened by wearing the contact lens, not even in an advanced stage of keratoconus, but is kept on a constant level or is improved.

Furthermore, the central optical zone may be rotationally symmetric or non-rotationally symmetric, depending on the particular requirement.

Figure 2:
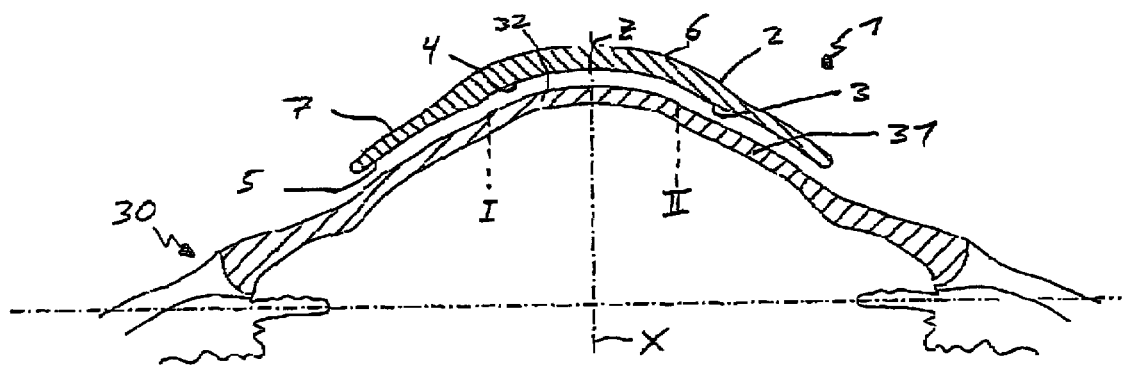

Further elements and appropriate features result from the description of exemplary embodiments by means of the accompanying drawings. In the figures, FIG. 1 is a schematic sectional view of a contact lens according to an embodiment;

FIG. 2 is a schematic sectional view of the contact lens of FIG. 1, placed on an eye with an irregular cornea; and FIGS. 3a to 3d are schematic views illustrating the curvature course of the central optical zone of the contact lens of FIG. 1 according to an exemplary embodiment.

Below, a first embodiment of the present invention will be described with reference made to FIG. 1.

As shown in FIG. 1, the contact lens 1 comprises a front surface 2 facing away from the eye of the person wearing the contact lens and a rear surface 3 facing the eye of the person wearing the lens. The rear surface 3 consists of a central optical zone 4 between lines A and B and at least one peripheral region 5 adjoining the central optical zone 4 all the way round at the outside. The front surface 2 comprises a central optical region 6 between lines C and D as well as a marginal region 7 adjoining the central optical region 6 at the outside. Essentially, the optical properties of the contact lens 1 are determined by the central optical zone 4 and the central optical region 6, whereas the peripheral region 5 and the marginal region 7 mainly serve the purpose of optimizing the seat on the eye of the person wearing the contact lens. The peripheral region 5 and the marginal region 7 can each be formed by a plurality of regions that are arranged adjacent to each other and, as shown in FIG. 1, comprise various curvature radiuses $r_1$, $r_2$, $r_3$, $r_4$, etc. Furthermore, the contact lens comprises a center Z through which extends a central optical axis X.

Below, the geometry of the central optical zone will be described on the basis of the schematic views shown in FIGS. 3a to 3d.

At first, the curvature course of known contact lenses is described on the basis of FIG. 3b. Where known contact lenses are concerned, the central optical zone 4 of the rear surface each comprises a spherical curvature course which is shown schematically in FIG. 3b. With this spherical curvature course, the curvature radius $r_{sph}$ remains constant over the entire diameter $d0_{sph}$ of the central optical zone 4'. Hence, the known contact lenses comprise a sagittal depth $s_{sph}$ which is defined by the curvature radius $r_{sph}$ and the diameter $d0_{sph}$ of the central optical zone 4'. In this case, the following applies to the sagittal depth: $Ssph = rsph - \sqrt{rsph^2 - (d0sph/2)^2}$.

Now, the curvature course of the illustrated embodiment of the present invention will be described on the basis of FIGS.

Figure 3A:
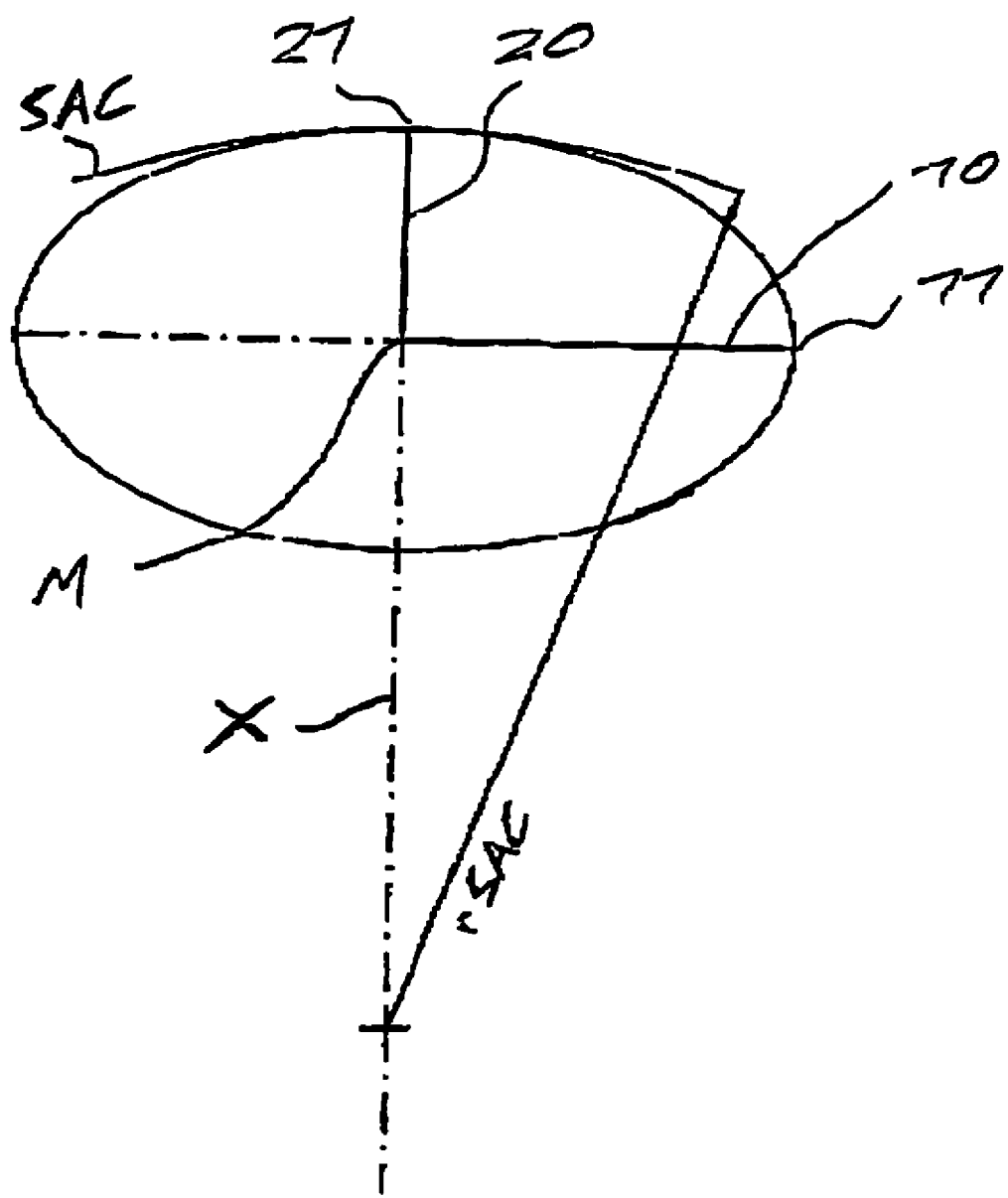

3c and 3a. In the illustrated embodiment, the central optical zone 4 of the rear surface comprises an elliptic-oblong curvature course. FIG. 3a shows an ellipse. Said ellipse comprises two main axes, that are a major axis 10 and a minor axis 20. The major axis 10 extends from the center point M of the ellipse to the main apex 11 while the minor axis 20 extends from the center point to the secondary apex 21, wherein the minor axis 20 is shorter than the major axis 10. The curvature of the ellipse at the secondary apex 21 corresponds to the curvature of a secondary apex curvature circle SAC having the radius $r_{SAC}$. As can be seen from FIG. 3a, the curvature of the elliptical surface increases with increasing tangential distance from the secondary apex 21, each being in excess of the curvature of the secondary apex curvature circle SAC. Therein, the curvature course is an elliptic-oblong one.

FIG. 3c schematically illustrates the central optical zone 4 with an elliptic-oblong curvature course. Over its entire diameter $d0_{ellip}$, the central optical zone 4 comprises an elliptic-oblong curvature course and, at its secondary apex 21 which coincides with the center Z of the central optical zone 4, has a curvature radius $r_{ellip\text{-}oblong}$ which corresponds to the radius $r_{SAC}$ of the secondary apex circle SAC. The sagittal depth $s_{ellip}$ of the central optical zone 4 according to the embodiment is defined by the eccentricity e of the basic ellipse and the diameter $d0_{ellip}$ of the central optical zone 4. Therein, the eccentricity of the basic ellipse preferably ranges from −0.3 to −0.9. The following applies to the sagittal depth and the elliptic-oblong course:

$$s_{ellip} = a \cdot (1 - \sqrt{1 - (d0ellip/2b)2})$$

wherein $$q = \frac{-e^2}{1-e^2}; \quad a = \frac{rSAC}{1-q};$$

and $b = a \cdot \sqrt{1-q}$.

FIG. 3d schematically shows the spherical curvature course of the central optical zone 4', as compared with the elliptic-oblong curvature course of the central optical zone according to the embodiment. Therein, the radius $r_{SAC}$ of the secondary apex circle SAC of the central optical zone 4 has been selected to be equal to the spherical radius $r_{sph}$ of the central optical zone 4' of the known contact lens ($r_{SAC} = r_{sph}$), while the diameters $d0_{ellip}$ and $d0_{sph}$ of the central optical zone 4 and the central optical zone 4' have been selected to be equal to each other ($d0_{sph} = d0_{ellip}$). As can be seen from FIG. 3d, the sagittal depth $S_{ellip}$ in the elliptic-oblong curvature course is in excess of the sagittal depth $s_{sph}$ in the spherical curvature course.

FIGS. 3b and 3c each are a merely two-dimensional sectional view of the central optical zones 4' and 4, whereas the real contact lenses naturally comprise a three-dimensional extension. According to the embodiment described, the central optical zones 4 and 4' each comprise a design that is rotationally symmetric in relation to the central optical axis X. The rear surface may be rotationally symmetric or non-rotationally symmetric, depending on the particular requirement.

The front surface 2 of the contact lens 1 has a spherical or aspherical, rotationally symmetric or toric design or a design of a combination thereof such that, together with the rear surface 3, it generates the necessary dioptric effect, thus resulting in optimum imaging conditions for the eye while the contact lens is worn.

Below, operation of the contact lens described will be illustrated in an exemplary embodiment based on FIG. 2.

As shown in FIG. 2, the contact lens 1 is placed onto the eye 30 of the person wearing said contact lens. In the illustrated instance, the cornea 31 comprises an irregularly curved central section 32 between lines I and II, which is caused by keratoconus in FIG. 2. Owing to its oblong curvature course, the central optical zone 4 bridges the irregularly curved section 32 and, with its peripheral region 5, the contact lens 1 rests on that region of the eye 30 that is positioned outside of the irregularly curved central section 32.

Owing to the oblong curvature course of the central optical zone 4, the contact lens 1, as compared with a contact lens made for a regularly curved cornea, does not comprise an increased curvature radius in the region of the center Z of the central optical zone 4, with the result that it is not necessary to design an increased optical effect of the contact lens and that the drawbacks disclosed above of the known contact lenses for keratoconus are not incurred. By the contact lens 1 allowing bridging of the irregularly curved region 32 of the cornea 31, the mechanical pressure and, hence, the load applied to the changed cornea are reduced, thus preventing the state of the cornea from deteriorating.

Further embodiments and variants

Although an elliptic-oblong curvature course of the central optical zone 4 has been described in the above embodiment, the contact lens may also comprise a different curvature course in this zone. Therein, however, it is important to ensure that the curvature course is not spherical but aspheric-oblong. That means that the central optical zone 4 comprises the least curvature, i.e. the largest curvature radius, in its center Z and that the curvature increases with increasing distance from the center Z, i.e. the curvature radius is becoming smaller, so that, with equal diameter do and equal curvature radius $r_z$ in the center Z, the sagittal depth of the central optical zone 4 is in excess of that of a spherical curvature course. Therein, the central optical zone 4 comprises an aspherical course over its entire surface.

With such a curvature course of the central optical zone 4, the curvature radius may, as has been described in the example above, be elliptic-oblong or the curvature course may be an aspherical curvature course of a higher order. In the simplest case, the rear surface 3 and its central optical zone 4 are, therein, designed rotationally symmetric about the central optical axis X. It is, however, possible to select a different curvature course, resulting from a combination of rotationally symmetric, toric, asymmetric, peripherally eccentric and/or quadrant-different designs.

The peripheral region 5 that is adjoining the central optical zone 4 may have a spherical design with a multitude of curves or an aspherical design, so that it can be fitted to the contour of the cornea in an optimum manner.

It is advantageous to design the central optical zone with a high degree of symmetry, if this is possible with the geometry of the eye to be treated, since this allows to achieve an optimum imaging behavior of the contact lens.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding European application No. 05018424.1, filed Aug. 24, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A rigid contact lens for correcting an irregularly curved cornea, comprising
a front surface (2) and a rear surface (3) which consists of a central optical zone (4) defining the optical properties of the contact lens and a peripheral zone (5) serving to seat the contact lens;
wherein the central optical zone (4) has such an aspherical rotationally symmetric or non-rotationally symmetric shape that, with equal central curvature radius in the center (Z) of the central optical zone (4), the sagittal depth ($s_{ellip}$) of the central optical zone (4) is increased as compared with a spherical optical zone, and wherein the curvature radius of the central optical zone (4) constantly decreases progressively or monotonically from the center (Z) of the central optical zone towards the periphery thereof.

2. A rigid contact lens according to claim 1, wherein the central optical zone (4) comprises the least curvature in its center (Z).

3. A rigid contact lens according to claim 1, wherein the central optical zone (4) comprises an aspheric-oblong curvature course.

4. A rigid contact lens according to claim 1, wherein the central optical zone (4) comprises an elliptical curvature course.

5. A rigid contact lens according to claim 4, wherein the eccentricity ranges from −0.3 to −0.9.

6. A rigid contact lens according to claim 1, wherein the entire rear surface (3) has a rotationally symmetric, non-rotationally symmetric, toric, asymmetric, peripherally eccentric or quadrant-different design or a design of a combination thereof.

7. A rigid contact lens according to claim 1, wherein the entire rear surface (3) has a rotationally symmetric design.

8. A rigid contact lens according to claim 1, wherein the peripheral region (5) has a spherical design with a multitude of curves or an aspherical design.

9. A rigid contact lens according to claim 1, wherein the peripheral region (5) is fitted to the contour of the cornea to be treated.

10. A rigid contact lens according to claim 1, wherein the front surface (2) of the contact lens is shaped according to a predefined dioptric effect.

11. A rigid contact lens according to claim 1, wherein the front surface (2) has a spherical, aspherical, rotationally symmetric or toric design or a design of a combination thereof.

12. The rigid contact lens of claim 1 wherein the central optical zone (4) has a non-rotationally symmetric shape.

13. The rigid contact lens of claim 1 wherein the irregularly curved cornea has an irregularly curved section and wherein the central optical zone bridges the irregularly curved section providing corrective optics for the irregularly curved section.

* * * * *